(12) United States Patent
Kitchin et al.

(10) Patent No.: US 11,679,223 B2
(45) Date of Patent: Jun. 20, 2023

(54) VENTILATOR AIRFLOW SPLITTER

(71) Applicant: Naval Information Warfare Center Pacific, San Diego, CA (US)

(72) Inventors: Tristan Charles Kitchin, San Diego, CA (US); Palmer Duston Hayward, San Diego, CA (US); Daniel Sean Jennings, San Diego, CA (US); Chandler James Petrovich Flynn, San Diego, CA (US); Annie Yu-Wen Lin, San Diego, CA (US); Eric William Goulet, San Diego, CA (US)

(73) Assignee: United States of America as represented by the Secretary of the Navy, Washington, DC (US)

(*) Notice: Subject to any disclaimer, the term of this patent is extended or adjusted under 35 U.S.C. 154(b) by 351 days.

(21) Appl. No.: 17/189,382

(22) Filed: Mar. 2, 2021

(65) Prior Publication Data
US 2022/0280742 A1    Sep. 8, 2022

(51) Int. Cl.
*A61M 16/00* (2006.01)
*A61M 16/08* (2006.01)
*A61M 16/20* (2006.01)
*B33Y 80/00* (2015.01)

(52) U.S. Cl.
CPC ........ *A61M 16/0875* (2013.01); *A61M 16/20* (2013.01); *A61M 2205/3334* (2013.01); *A61M 2207/00* (2013.01); *B33Y 80/00* (2014.12)

(58) Field of Classification Search
CPC .............. A61M 16/0875; A61M 16/20; A61M 2205/3334; A61M 2207/00; B33Y 80/00
See application file for complete search history.

(56) References Cited

U.S. PATENT DOCUMENTS

2017/0128693 A1    5/2017 Darowski et al.

OTHER PUBLICATIONS

G. Neyman, C.B. Irvin, "A Single Ventilator for Multiple Simulated Patients to Meet Disaster Surge", Society for Academic Emergency Medicine, vol. 13, No. 11, pp. 1246-1249, 2006, https://onlinelibrary.wiley.com/doi/epdf/10.1197/i.aem.2006.05.009.
R.D. Branson, T.C. Blakeman, B.RH. Robinson, J.A. Johannigman, "Use of a Single Ventilator to Support 4 Patients: Laboratory Evaluation of a Limited Concept", Respiratory Care, vol. 57, No. 3, pp. 399-403, 2012, http://rc.rcjournal.com/content/respcare/57/3/399.full.pdf.

*Primary Examiner* — Steven O Douglas
(74) *Attorney, Agent, or Firm* — Naval Information Warfare Center, Pacific; Kyle Eppele; Matthew D. Pangallo

(57) ABSTRACT

A ventilator airflow splitter is described herein that includes two to four connectors extending axially through two to four channels starting from a port insert of a single inlet connector and terminating at a port of each of the two to four connectors. The two to four connectors merge into the single inlet connector where the single inlet connector includes an internal cross-splitter individually dividing each of the two to four connectors internally, thereby separating the airflow between each of the two to four connectors such that the air is incapable of moving between connectors. The ventilator airflow splitter also includes gussets where each of the two to four connectors have a gusset individually attached and the gussets merge at the single inlet connector. Each of the two to four connectors are configured to be operatively connected to medical equipment or a ventilator at the ports and the port insert of the single inlet connector.

21 Claims, 4 Drawing Sheets

VENTILATOR AIRFLOW SPLITTER

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND

Ventilators provide mechanical ventilation by moving breathable air into and out of the lungs to allow patients to breathe who are otherwise unable to. Ventilators range from computerized electronically controlled machines to manual hand-operated bag valve masks. Generally, ventilators include inspiratory and expiratory sections with a single tube for each. The tubes are connected to the machines or bags at one end and a valve or tubing connected to the patient at the other end.

DESCRIPTION OF THE DRAWINGS

Features and advantages of examples of the present disclosure will be apparent by reference to the following detailed description and drawings, in which reference numerals correspond to similar, but in some instances, not identical, components. Reference numerals or features having a previously described function may or may not be described in connection with other drawings in which they appear.

DETAILED DESCRIPTION

Ventilators are typically used on one patient at a time with a single tube for inhalation and a single tube for exhalation. However, in certain situations where there is a shortage of ventilators, attempts have been made to use a single ventilation device on multiple patients. The single ventilation device splits the inhalation and exhalation tube into two or more tubes depending on the additional number of patients for each device. These attempts have had a number of issues. In some instances, the tube splitter is multiple pieces connected together to split the inhalation and exhalation tubes into two inhalation and two exhalation tubes. Since there are multiple pieces connected together, there are additional locations where airflow leakage can occur. In addition, some of the pieces used to split the tubes include 90° bends in the tube, which causes air turbulence, and a reduction in airflow. Furthermore, when splitting a ventilator, problems can arise with regulating airflow to each individual patient since every patient is connected to a single ventilator.

The ventilator airflow splitter herein divides a ventilator between multiple patients by adding an airflow splitter to the inhalation, exhalation, or both the inhalation and the exhalation connectors. The ventilator airflow splitter herein is constructed as a single piece rather than multiple pieces fit together. As a result, there is no airflow leakage or diminished airflow capacity in the ventilator when split between multiple patients. Moreover, the ventilator airflow splitter herein includes bends that are 45° or less. This allows the air to flow smoothly through the splitter without causing air turbulence or a reduction in airflow.

In an example, the ventilator airflow splitter described herein includes two to four connectors extending axially through two to four channels starting from a port insert of a single inlet connector and terminating at a port of each of the two to four connectors. The two to four connectors merge into the single inlet connector where the single inlet connector includes an internal cross-splitter individually dividing each of the two to four connectors internally, thereby separating the airflow between each of the two to four connectors such that the air is incapable of moving between connectors. The ventilator airflow splitter also includes gussets where each of the two to four connectors have a gusset individually attached and the gussets merge at the single inlet connector. Each of the two to four connectors are configured to be operatively connected to medical equipment at the ports and the port insert of the single inlet connector.

Figure 1:
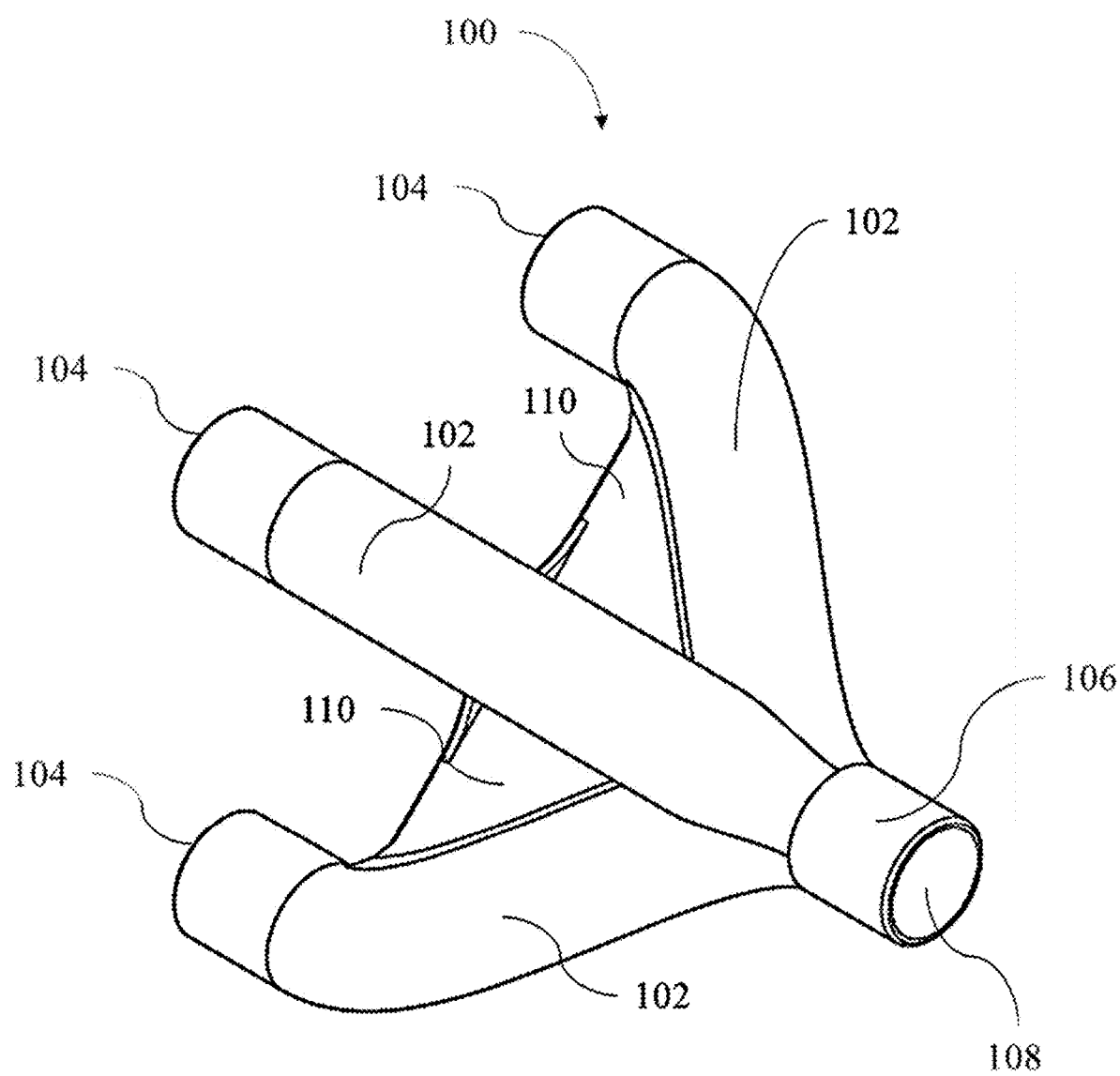
FIG. 1 is a generalized view of an example of the ventilator airflow splitter described herein.

Referring now to FIG. 1, a generalized view of an example of the ventilator airflow splitter 100 herein is shown. FIG. 1 shows the ventilator airflow splitter 100 that includes four connectors 102. In some examples, the ventilator airflow splitter 100 can include a range of two to four connectors 102. In other examples, the ventilator airflow splitter 100 may be connected in-series with each ventilator airflow splitter 100 including two to four connectors 102 to include the maximum amount of connectors 102 possible (i.e., a plurality of connectors 102) while allowing a ventilator machine to maintain suitable performance. In FIG. 1, the four connectors 102 extend axially as four channels starting from a port insert 108 of a single inlet connector 106 and terminating at a port 104 of each individual connector 102. Each connector 102 has a port 104 that is configured to be operatively connected to medical equipment (e.g., hoses that connect to the patient or a ventilator) or a valve, which is described in greater detail below. Furthermore, the port insert 108 of the single inlet connector 106 is also configured to be operatively connected to medical equipment (e.g., hoses that connect to the patient or a ventilator) or a valve. Regardless of whether there are two or more connectors 102, when the connectors 102 extend axially as channels, every channel has an angle 112 between the center of an individual connector 102 and the center of the single inlet connector 106 of equal to or less than 45°. The angle 112 is shown in FIG. 1 as a visual aid, but is not drawn to scale. In addition, the distance between outside diameters of the ports 104 of each connector 102 must be equal to or greater than 2.54 cm (1 in).

Referring back to FIG. 1, the ventilator airflow splitter 100 also includes gussets 110 attached to each connector 102. The gussets 110 form a rigid support for each individual connector 102 and merge at the single inlet connector 106 to provide support to withstand radial and twisting loads from attaching and detaching medical equipment (e.g., additional hoses going to a patient or ventilator). In FIG. 1, there are four gussets 110 with one gusset 110 as a part of each connector 102. In an example, a gusset 110 is a part of every connector 102 and the gussets 110 merge at the single inlet connector 106. Regardless of the number of connectors 102, every connector 102 includes a gusset 110. In an example, the connectors 102 and the gussets 110 form a single continuous piece without any sealed joints. For example, if the ventilator airflow splitter 100 has two to four connectors 102, then the two to four connectors 102 and the two to four gussets 110 form a single piece without any sealed joints.

Figure 2A:
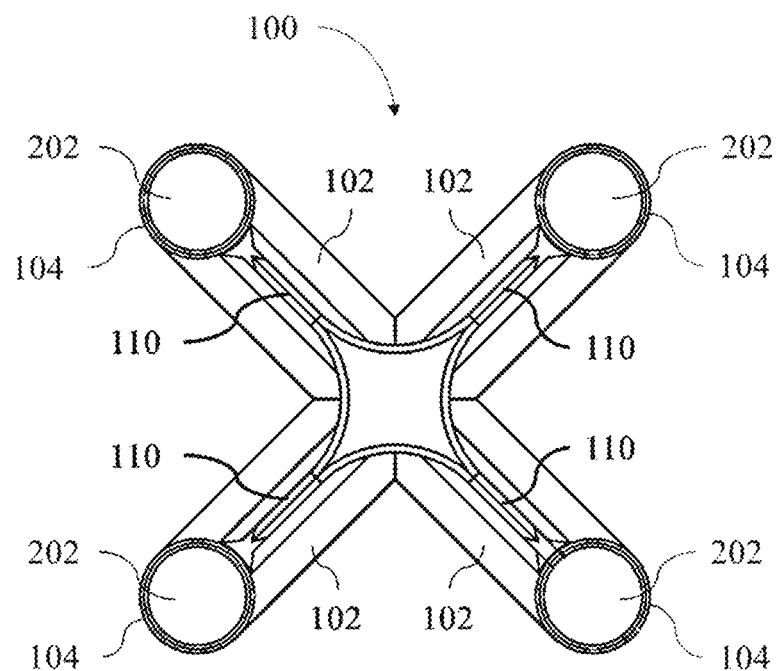
FIG. 2A is a bottom view of the example of the ventilator airflow splitter described herein.

Referring now to FIG. 2A, another general view of the ventilator airflow splitter 100 is shown. FIG. 2A is a view from the bottom perspective viewing directly into the ports 104. In FIG. 2A, there are four channels 202 for each connector 102. The gussets 110 are shown attached to each connector 102 and merge at the single inlet connector 106 (not shown in FIG. 2A). In FIG. 2A, there are four connectors 102, gussets 110, and channels 202. However, as previously stated herein, there may be two to four connectors 102, gussets 110, and channels 202 for a single ventilator airflow splitter 100 or for each individual ventilator airflow splitter 100 connected in-series with additional airflow ventilator splitters 100 with the maximum amount limited only by the ventilator machine maintaining suitable performance.

Figure 2B:
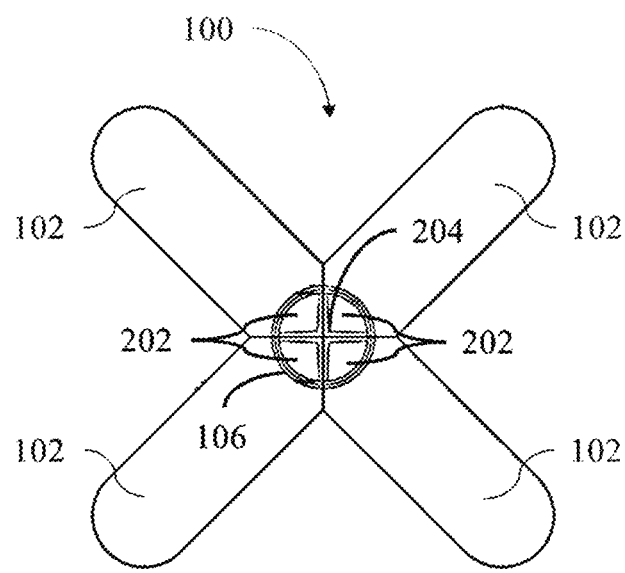
FIG. 2B is a top view of the example of the ventilator airflow splitter described herein.

Referring to FIG. 2B, a top view of an example of the ventilator airflow splitter 100 is shown. In FIG. 2B, a cross-section of the single inlet connector 106 is shown. Within the single inlet connector 106, there is an internal cross-splitter 204, which individually divides the airflow internally between each connector 102 into four channels 202. The airflow is divided such that that the air is incapable of moving between connectors 102. In FIG. 2B, each of the four channels 202 created by the internal cross-splitter 204 merges into the side of each connector 102 to prevent air from moving between channels 202 within each connector 102. In another example, if the ventilator airflow splitter 100 has two or three connectors 102, then the internal cross-splitter 204 will split the airflow into two or three channels 202, respectively.

Figure 3A:
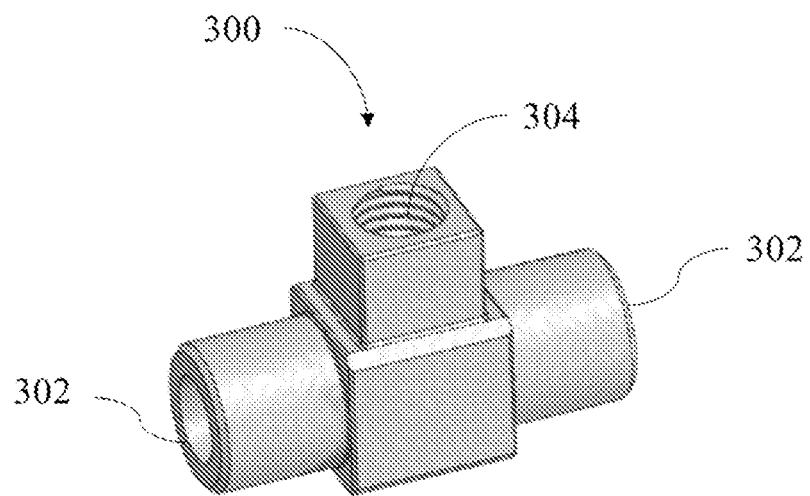
FIG. 3A-3B are examples of the main body of a valve and the valve stem of a valve described herein.
Figure 3B:
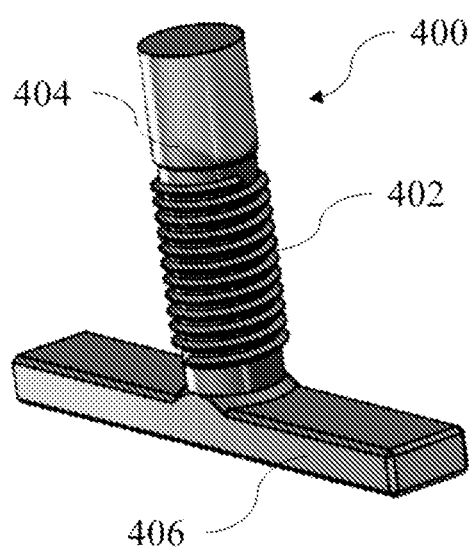

In an example, the ventilator airflow splitter 100 herein may also include valves that connect to the ports 104 of each connectors 102 or the port insert 108 of the single inlet connector 106. In this example, the valves are configured to be operatively connected to medical equipment rather than the ports 104 being configured to be operatively connected directly to the medial equipment. For example, the valves may be specifically designed to fit 22 mm tubing that is standardized for respiratory or ventilator tubing. In another example, a valve are configured to be operatively connected to medical equipment, such as ventilator tubing, rather than the port insert 108. FIG. 3A and FIG. 3B show an example of the valve that may be connected to the ports 104. In FIG. 3A, the main body 300 of the valve is shown. The main body 300 includes valve port inserts 302 at both ends where a port 104 of the ventilator airflow splitter 100 can be inserted at one valve port inserts 302 and medical equipment can be inserted and attached at the other valve port inserts 302. In addition, the main body 300 includes a valve stem insert 304 where the valve stem 400 can be screwed into the main body 300 of the valve to reduce the gas flowrate or unscrewed to increase the gas flowrate. The main body 300 of the valve may be a separate piece that is configured to be operatively connected to a port 104 or the main body 300 may be forms as part of the entire ventilator airflow splitter 100 along with the connectors 102 and the gussets 110 as a single piece without any sealed joints. In some examples, there is the main body 300 of the valve is attached to every connector 102. In another example, the main body 300 of the valve may only be attached to some, but not all, of the connectors 102.

In FIG. 3B, an example of the valve stem 400 is shown. The valve stem 400 includes threads 402 along a shaft 404. In the example shown in FIG. 3B, the valve stem 400 has a handle 406 that allows a user to manually screw or unscrew the valve stem 400 to adjust the flowrate of the gas to a patient. In another example, the valve stem 400 can be automated or electronically controlled to adjust the flowrate of gas to a patient.

Figure 4:
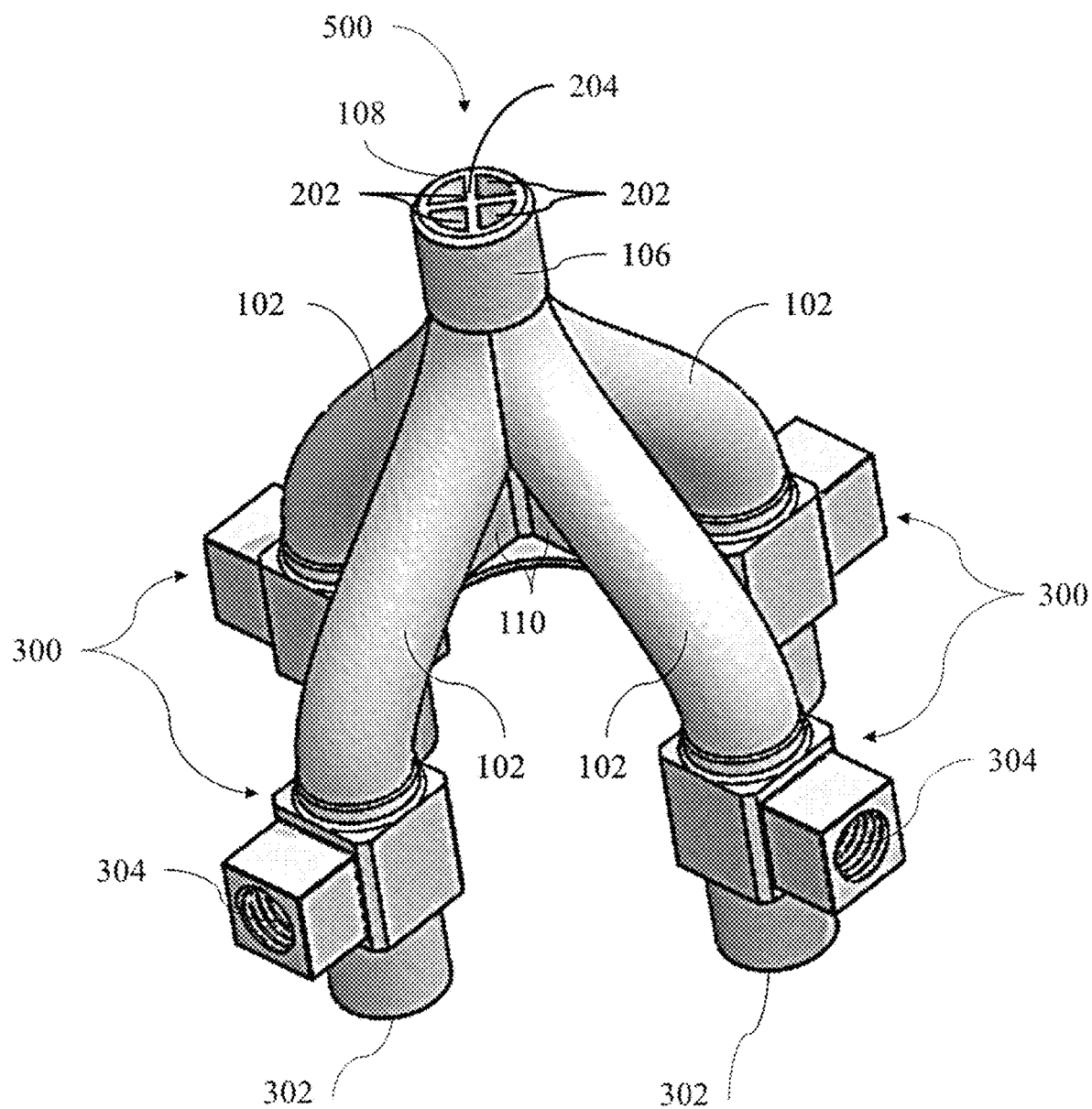
FIG. 4 is another example of the ventilator airflow splitter described herein.

Referring now to FIG. 4, an example of the ventilator airflow splitter including the main body 300 of the valves 500 is shown. In FIG. 4, the main body 300 of the valves is permanently attached. The ventilator airflow splitter with valves 500 includes four connectors 102, four gussets 110 (only two visible), and four main bodies 300 of valves as a single piece without any sealed joints. Additionally, in this example, the internal cross-splitter 204 is shown in the port insert 108 of the single inlet connect 106 with four distinct channels 202 for each connector 102. Similar to FIG. 1, the connectors 102 extend axially as four channels 202 starting from a port insert 108 of a single inlet connector 106 and terminating at the valve port insert 302 on the main body 300 of each individual valve. In the example in FIG. 4, each connector 102 has the main body 300 of a valve attached and configured to be operatively connected to medical equipment at the open valve port insert 302. In addition, as previously described herein, each connector 102 has an angle 112 (not shown in FIG. 4) between the center of an individual connector 102 and the center of the single inlet connector 106 of equal to or less than 45°.

It is noted that any suitable type of material may be used to make any examples of the ventilator airflow splitter (100, 500) described herein. Furthermore, the size of the components, such as the connectors 102, ports 104, single inlet connector 106, port insert 108, gussets 110, channels 202, internal cross-splitter 204, main body 300 of the valve, valve port insert 302, valve stem insert 304, or combinations thereof, in the ventilator airflow splitter (100, 500) described herein may be adjusted to fit specific ventilators or medical equipment that the ventilator airflow splitter is being attached thereto.

Regarding the method of making the ventilator airflow splitters, any example of the ventilator airflow splitter (100, 500) previously disclosed herein can be made using a 3D printer. In one example, any known 3D printer may be used to print the ventilator airflow splitters herein. In another example, a stereolithography (SLA) printer may be used to print the ventilator airflow splitter (100, 500) and the valve including the main body 300 and the valve stem 400. The ventilator airflow splitter (100, 500) is printed in the direction of the Z-axis starting with either the ports 104 or the main body 300 of the valves. Then, each connector 102 including the channels 202 are printed ending with the single inlet connector 106 and the port insert 108. In addition to printing the actual components, external support material is also printed to provide an elevated platform during the printing process for components being built that do not contact the build plate. After the print is complete, the external support material can be removed, thereby forming the ventilator airflow splitter.

The 3D printing can use a digital file containing the design the of the ventilator airflow splitters herein. This allows the ventilator airflow splitter design to be digitally transferable worldwide and printed within a very short amount of time. The digital file may be created using any known software used for 3D printing. For example, the digital file may be a .STL file. Additionally, any suitable type of material used to 3D print and make the ventilator airflow splitter herein may be used. The size of the components, such as the connectors 102, ports 104, single inlet connector 106, port insert 108, gussets 110, channels 202, internal cross-splitter 204, main body 300 of the valve, valve port insert 302, valve stem insert 304, or combinations thereof, in the ventilator airflow splitter described herein may be adjusted to fit specific ventilators or medical equipment that the ventilator airflow splitter is being attached thereto.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of a list should be construed as a specific equivalent of any other member of the same list merely based on their presentation in a common group without indications to the contrary.

Unless otherwise stated, any feature described herein can be combined with any aspect or any other feature described herein.

Reference throughout the specification to "one example", "another example", "an example", means that a particular element (e.g., feature, structure, and/or characteristic) described in connection with the example is included in at least one example described herein, and may or may not be present in other examples. In addition, the described elements for any example may be combined in any suitable manner in the various examples unless the context clearly dictates otherwise.

The ranges provided herein include the stated range and any value or sub-range within the stated range. For example, a range from about 0.1° to about 45° should be interpreted to include not only the explicitly recited limits of from about 0.1° to about 45°, but also to include individual values, such as 3°, 17°, 33.5°, etc., and sub-ranges, such as from about 15° to about 35°, etc.

In describing and claiming the examples disclosed herein, the singular forms "a", "an", and "the" include plural referents unless the context clearly dictates otherwise.

What is claimed is:

1. A ventilator airflow splitter, comprising:
   at least two connectors extending axially through at least two channels starting from a port insert of a single inlet connector and terminating at a port of each of the at least two connectors, wherein the at least two connectors merge into the single inlet connector where the single inlet connector includes an internal cross-splitter individually dividing each of the at least two connectors internally, thereby separating the airflow between each of the at least two connectors such that the air is incapable of moving between connectors;
   gussets wherein each of the at least two connectors have gussets individually attached and the gussets merge at the single inlet connector; and
   wherein each of the at least two connectors are configured to be operatively connected to medical equipment at the ports and at the port insert of the single inlet connector.

2. The ventilator airflow splitter of claim 1, wherein the at least two channels have an angle between a center of an individual connector and a center of the single inlet connector of equal to or less than 45°.

3. The ventilator airflow splitter of claim 1, wherein the at least two connectors and the gussets are a single piece without any sealed joints.

4. The ventilator airflow splitter of claim 1, further comprising valves that connect to the ports of each of the at least two connectors, wherein the valves are configured to be operatively connected to medical equipment.

5. The ventilator airflow splitter of claim 4, wherein each valve includes a main body and a valve stem where the valve stem screws into the main body of the valve to adjust a flow rate of gas.

6. The ventilator airflow splitter of claim 5, wherein the main body and the valve stem of each valve are individual pieces and the main body of each valve is configured to be operatively connected to the ports.

7. The ventilator airflow splitter of claim 5, wherein the at least two connectors, the gussets, and the main body of the valves are a single piece without any sealed joints.

8. The ventilator airflow splitter of claim 4, wherein each valve includes a main body and a valve stem where the valve stem is electronically controlled to adjust a flowrate of gas.

9. The ventilator airflow splitter of claim 1, wherein a distance between an outside diameter of any of the ports is equal to or greater than 2.54 cm.

10. A method of making a ventilator airflow splitter, comprising:
    3D printing the ventilator airflow splitter with the following components:
    i) at least two connectors extending axially through at least two channels starting from a port insert of a single inlet connector and terminating at a port of each of the at least two connectors, wherein the at least two connectors merge into the single inlet connector where the single inlet connector includes an internal cross-splitter individually dividing each of the at least two connectors internally, thereby separating the airflow between each of the at least two connectors such that the air is incapable of moving between connectors;
    ii) gussets wherein each of the at least two connectors have gussets individually attached and the gussets merge at the single inlet connector; and
    iii) external support material; and
    removing the external support material, thereby forming the ventilator airflow splitter.

11. The method of claim 10, wherein the at least two channels are printed with an angle between a center of an individual connector and a center of the single inlet connector of equal to or less than 45°.

12. The method of claim 10, wherein the at least two connectors and the gussets are printed as a single piece without any sealed joints.

13. The method of claim 10, further comprising 3D printing valves that connect to the ports at each of the at least two connectors.

14. The method of claim 13, wherein each valve includes a main body and a valve stem where the valve stem screws into the main body of the valve to adjust a flow rate of gas.

15. The method of claim 14, wherein the main body and the valve stem of each valve are printed separately as individual pieces and are configured to be operatively connected to the ports.

16. The method of claim 15, wherein the at least two connectors, the gussets, and the main body of each valve are printed as a single piece without any sealed joints.

17. The method of claim 10, wherein the 3D printing occurs in a direction of a Z-axis.

18. The method of claim 10, wherein the 3D printing uses a digital file to print the ventilator airflow splitter.

19. The method of claim 10, wherein each valve includes a main body and a valve stem where the valve stem is electronically controlled to adjust a flowrate of gas.

20. The method of claim 10, wherein a distance between an outside diameter of any of the ports is equal to or greater than 2.54 cm.

21. A ventilator airflow splitter, comprising:
- connectors, wherein there are two, three, or four connectors that extending axially through channels starting from a port insert of a single inlet connector and terminating at a port of each of the connectors, wherein the connectors merge into the single inlet connector where the single inlet connector includes an internal cross-splitter individually dividing each of the connectors internally, thereby separating the airflow between each of the connectors such that the air is incapable of moving between connectors;
- gussets wherein each of the connectors have gussets individually attached and the gussets merge at the single inlet connector; and
- wherein each of the connectors are configured to be operatively connected to medical equipment at the ports and at the port insert of the single inlet connector.

* * * * *